(12) United States Patent
Gjermansen et al.

(10) Patent No.: US 11,414,814 B2
(45) Date of Patent: Aug. 16, 2022

(54) POLYPEPTIDES

(71) Applicant: Novozymes A/S, Bagsvaerd (DK)

(72) Inventors: Morten Gjermansen, Greve (DK); Lone Baunsgaard, Helsingor (DK); Fabian Barrientos Garcia, Birkeroed (DK)

(73) Assignee: Novozymes A/S, Bagsvaerd (DK)

( * ) Notice: Subject to any disclaimer, the term of this patent is extended or adjusted under 35 U.S.C. 154(b) by 382 days.

(21) Appl. No.: 16/647,601

(22) PCT Filed: Sep. 21, 2018

(86) PCT No.: PCT/EP2018/075617
§ 371 (c)(1),
(2) Date: Mar. 16, 2020

(87) PCT Pub. No.: WO2019/057902
PCT Pub. Date: Mar. 28, 2019

(65) Prior Publication Data
US 2020/0263350 A1     Aug. 20, 2020

(30) Foreign Application Priority Data
Sep. 22, 2017 (EP) .................................. 17192588

(51) Int. Cl.
*C12N 9/22* (2006.01)
*D06M 16/00* (2006.01)

(52) U.S. Cl.
CPC ............. *D06M 16/003* (2013.01); *C12N 9/22* (2013.01); *D06M 2200/45* (2013.01); *D06M 2200/50* (2013.01)

(58) Field of Classification Search
CPC ................................ C12N 9/22; C12N 9/2411
See application file for complete search history.

(56) References Cited

FOREIGN PATENT DOCUMENTS

| EP | 3388507 A1 | 10/2018 |
|---|---|---|
| WO | 2015/181287 A1 | 12/2015 |
| WO | 2017/060505 A1 | 4/2017 |
| WO | 2017/162836 A1 | 9/2017 |
| WO | 2018/011276 A1 | 1/2018 |

*Primary Examiner* — Tekchand Saidha
(74) *Attorney, Agent, or Firm* — Yoshimi Barron

(57) ABSTRACT

The present invention relates to novel polypeptides having nuclease activity and the use and methods for preventing or reducing creases of a fabric; a composition comprising such polypeptide. The invention further related to polynucleotide encoding polypeptides having nuclease activity.

7 Claims, No Drawings
Specification includes a Sequence Listing.

POLYPEPTIDES

CROSS-REFERENCE TO RELATED APPLICATIONS

This application is a 35 U.S.C. 371 national application of international application no. PCT/EP2018/075617 filed Sep. 21, 2018 which claims priority or the benefit under 35 U.S.C. 119 of European application no. 17192588.6 filed Sep. 22, 2017, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to a novel nuclease, a composition comprising the nuclease, the use in cleaning processes and a method for treating a fabric comprising the nuclease.

BACKGROUND OF INVENTION

Cleaning processes such as laundry of fabrics involve application of detergents and some degree of mechanical stress to the fabric being cleaned. In addition to chemical ingredients such as surfactants, builders etc. most detergents comprise enzymes such as protease, amylases and lipases targeting specific stain removal of e.g. proteinaceous, starch and grease stains. In addition to soiling fabrics such as textile items are prone to deformations in the fabric before, during and after laundering. These deformations are non-permanent and can be removed by ironing the fabric however the fabric must be ironed upon each occasion of laundering. The deformations are commonly termed creases or wrinkles.

The present invention provides nucleases particularly useful for anti-creases and softening of fabrics and for use in compositions and methods for improving the properties of fabrics.

SUMMARY OF THE INVENTION

The present invention relates to the use of a nuclease to treat a fabric to provide improved softness and/or ease of ironing and/or anti-crease properties. In one embodiment, the nuclease has RNase and DNase activity.

The invention further relates to a composition comprising nuclease having DNase and RNase activity, wherein the composition further comprises;
  (a) one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
  (b) optionally one or more enzyme, preferably selected from proteases, amylases or lipases,
  (c) optionally one or more surfactant, preferably selected from anionic and nonionic surfactants, and
  (d) optionally one or more polymers.

The invention further relates to a method for modifying a fabric material comprising (a) treating the fabric with a composition comprising a nuclease; (b) under conditions leading to a modified fabric, wherein the modified fabric possesses a fabric improvement compared to the unmodified fabric.

The invention further relates to a method for preventing or reducing creases and/or improving softness of a fabric comprising the steps of:
  a) contacting the fabric with a composition of the invention or nuclease having DNase and RNase activity; and
  b) optionally rinsing the fabric.

DEFINITIONS

As used herein, the singular forms "a", "an", and "the" are intended to include the plural forms as well, unless the context clearly indicates otherwise.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Anti-wrinkle and Anti-crease: In the context of the present invention, the terms "crease" and "wrinkle" and related terms, such as "anti-crease" and "anti-wrinkle", refer to non-permanent deformations in fabrics, such as textiles which can be removed by flattening at elevated temperature and moisture (e.g. by ironing). The terms are used interchangeably herein.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulosic textile material: The term "cellulosic textile material" means any cellulosic textile material including yarns, yarn intermediates, fibers, threads, non-woven materials, natural materials, synthetic materials, and any other textile material, fabrics made of these materials and products made from the fabrics (e.g., garments and other articles). The textile material may be in the form of knits, wovens, denims, non-wovens, felts, yarns, and towelling. The textile material is cellulose-based such as natural cellulosic material, including cotton, flax/linen, jute, ramie, sisal or coir or man-made cellulosic material (e.g., originating from wood pulp) including viscose/rayon, ramie, cellulose acetate fibers (tricell), lyocell or blends thereof. The cellulosic textile material may also be blends of cellulose based and non-cellulose based fibers, wherein the non-cellulose based material is natural polyamides including wool, camel, cashmere, mohair, rabbit and silk or a synthetic polymer such as nylon, aramid, polyester, acrylic, polypropylene and spandex elastane, or a blend thereof. Examples of blends are blends of cotton and/or rayon/viscose with one or more companion materials such as wool, synthetic fiber (e.g., polyamide fiber, acrylic fiber, polyester fiber, polyvinyl alcohol fiber, polyvinyl chloride fiber, polyurethane fiber, polyurea fiber, aramid fiber), and/or cellulose-containing fiber (e.g., rayon/viscose, ramie, flax/linen, jute, cellulose acetate fiber, lyocell).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Detergent components: the term "detergent components" is defined herein to mean the types of chemicals which can be used in detergent compositions. Examples of detergent components are alkalis, surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants and solubilizers.

Detergent Composition: the term "detergent composition" refers to compositions that find use in the removal of undesired compounds from items to be cleaned, such as textiles. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pre-treatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fabric: The term "fabric" includes any textile material such as yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). The fabric or textile can also be made of microfiber, which is synthetic fiber made from polyesters, polyamides (e.g., nylon, Kevlar, Nomex, trogamide), or a conjugation of polyester, polyamide, and polypropylene (Prolen). Fabric may be conventional washable laundry, for example stained household laundry. When the term fabric or garment is used, it is intended to include textiles as well.

Fabric improvement: The term "fabric improvement" or "textile improvement" means a benefit not directly related to catalytic stain removal or prevention of re-deposition of soils. Examples of such benefits are anti-backstaining, anti-pilling, anti-shrinkage, anti-wear, anti-crease, improved color appearance, fabric softness, improved shape retention, flame or chemical resistance, anti-odor, anti-UV, water-repellency, improved association between non-cellulosic and cellulosic textiles, improved static control, improved hand or texture, resistance to chemical, biological, radiological or physical hazard, and/or improved tensile strength. Prevention or reduction of dye transfer from one textile to another textile or another part of the same textile is termed anti-backstaining (also termed dye transfer inhibition). Removal of protruding or broken fibers from a textile surface to decrease pilling tendencies or remove already existing pills or fuzz is termed anti-pilling. Coating or reincorporation or smoothing of protruding or broken fibers is also termed anti-pilling. Prevention of or reduction of a decrease in dimensional size is termed anti-shrinkage. Prevention of or repair of abrasion is termed anti-wear. Prevention of creases, recovery of textile from creasing/wrinkling, smoothness of seams, and/or retention of creases after repeated home laundering is termed "anti-wrinkle" or anti-crease. Improvement of the textile-softness or reduction of textile stiffness is termed improved fabric softness. Color clarification of a textile, or enhanced colour fastness to laundering, perspiration, light, chlorine and non-chlorine bleach, heat, or light at high temperature is termed improved color appearance. Resistance to dimensional size change or dimensional size change during home laundering is termed improved shape retention. Elevated combustion temperature or resistance to burning or melting at high temperatures is termed flame resistance. Resistance to chemical reactions, solubilisation or degradation in the presence of chemical solvents, acid or alkali is termed chemical resistance. Resistance to adsorption or prevention of the retention of odorous compounds, particularly short chain fatty acids or low vapor pressure organic compounds is termed anti-odor. Opacity to and prevention or repair of oxidative damage caused by UV irradiation is termed anti-UV. Decreased retention of water, or resistance to wetting is termed water repellence. An increase in resistance to induced electrostatic charge of a textile, or increase in decay rate of an induced electrostatic charge in a textile is termed improved static control. Resistance to elongation under force or augmentation of breaking force is termed improved tensile strength.

Fragment: The term "fragment" means a polypeptide having one or more (e.g., several) amino acids absent from the amino and/or carboxyl terminus of a mature polypeptide or domain; wherein the fragment has nuclease activity. In one aspect, a fragment contains at least 220 amino acid residues (e.g., amino acids 10 to 230 of SEQ ID NO: 2), at least 210 amino acid residues (e.g., amino acids 10 to 220 of SEQ ID NO: 2), or at least 200 amino acid residues (e.g., amino acids 20 to 220 of SEQ ID NO: 2).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 231 of SEQ ID NO: 2. Amino acids −31 to −1 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. In one aspect, a mature polypeptide contains up to 220 amino acid residues (e.g., amino acids 5 to 225 of SEQ ID NO: 2), up to 210 amino acid residues (e.g., amino acids 10 to 220 of SEQ ID NO: 2), or up to 200 amino acid residues (e.g., amino acids 10 to 210 of SEQ ID NO: 2).

Mature polypeptide coding sequence: The term "mature polypeptide coding sequence" means a polynucleotide that encodes a mature polypeptide having nuclease activity. In one aspect, the mature polypeptide coding sequence is nucleotides 94 to 786 of SEQ ID NO: 1 and nucleotides 1 to 93 of SEQ ID NO: 1 encode a signal peptide.

Nuclease: The term "nuclease" includes nucleodepolymerase and polynucleotidase, and is an enzyme capable of cleaving the phosphodiester bonds between monomers of nucleic acids.

Nucleases cleave single and double stranded polynucleotides. There are two primary classifications based on the locus of activity. Exonucleases digest nucleic acids from the ends.

Endonucleases act on regions in the middle of target molecules. Nucleases are further subcategorized as deoxyribonucleases and ribonucleases. The former acts on DNA, the latter on RNA. The term "DNase" (deoxyribonuclease) means a polypeptide with DNase activity that catalyzes the hydrolytic cleavage of phosphodiester linkages in the DNA backbone, thus degrading DNA. DNase activity may be determined according to the procedure described in the Assay I or Assay II. The term "RNase" (ribonuclease) means a polypeptide having RNase activity that catalyzes the degradation of RNA into smaller components. RNase activity may be determined according to the procedure described in the Assay III. In one aspect, a nuclease for use according to the invention has DNase activity. In one aspect, the nuclease has RNase activity. In a preferred aspect, the nuclease has DNase and RNase activity, wherein the two activities may be determined as described in Assay I or II and III respectively. A nuclease usable according to the invention preferably has at least 20%, e.g., at least 40%, at least 50%, at least 60%, at least 70%, at least 80%, at least 90%, at least 95%, but less than 100% DNase activity of the total nuclease activity. A nuclease usable according to the invention preferably has at least 20%, e.g., at least 40%, at least 50%, at least 60%, at least 70%, at least 80%, at least 90%, at least 95%, but less than 100% RNase activity of the total nuclease activity. "Total nuclease activity" is defined in the present context as the sum of DNase and RNase activity when measured as described in Assay I or II and III respectively. Thus, a preferred nuclease for use according to the invention has DNase and RNase activity. "Nuclease activity" is defined as polypeptides having either DNase or RNase activity in the present context a nuclease for use according to the invention has both DNase and RNase activity as determined in the Assays I, or II and III respectively.

According to one aspect, the ratio of RNase versus DNase activity is ranging from 1:10 to 10:1, preferably 1:2 to 2:1 or preferably is 1:1, 2:1, 3:1, 4:1, 5:1 or 1:2, 1:3, 1:4, 1:5.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences may be determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment).

Variant: The term "variant" means a polypeptide having Nuclease activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is intended to mean the solution or mixture of water and detergents optionally including enzymes used for laundering textiles, for hard surface cleaning or for dishwashing.

DETAILED DESCRIPTION OF THE INVENTION

The present invention relates to nucleases and compositions and methods comprising nucleases. The invention further relates to a nuclease and the use in cleaning processes and compositions. In particular, the nucleases of the invention are suitable for improving properties of fabrics such as cellulosic and/or non-cellulosic textile material. Non-limiting examples of such properties include anti-pilling, anti-shrinkage, anti-wear, color appearance, fabric softness, shape retention and/or static control. The present invention relates to the use of nucleases, compositions and methods comprising nucleases. A nuclease according to the present invention have DNase and RNase activity. The nuclease of the invention comprises at least one property suitable for cleaning processes. In one aspect, such property is anti-crease and/or softness.

In an embodiment, the present invention relates to polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have nuclease activity. In one aspect, the polypeptides differ by up to 10 amino acids, e.g., 1, 2, 3, 4, 5, 6, 7, 8, 9, or 10, from the mature polypeptide of SEQ ID NO: 2.

A polypeptide of the present invention preferably comprises or consists of the amino acid sequence of SEQ ID NO: 3 or an allelic variant thereof; or is a fragment thereof having nuclease activity. In another aspect, the polypeptide comprises or consists of SEQ ID NO 3 or the mature polypeptide of SEQ ID NO: 2. In another aspect, the polypeptide comprises or consists of amino acids 1 to 231 of SEQ ID NO: 2.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10.

One aspect of the invention relates to a polypeptide having nuclease activity, selected from the group consisting of:

(a) a polypeptide having at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;

(b) a polypeptide encoded by a polynucleotide having at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;

(c) a variant of the mature polypeptide of SEQ ID NO: 2 comprising a substitution, deletion, and/or insertion at one or several positions, wherein the variant has nuclease activity; and (d) a fragment of the polypeptide of (a), (b) or (c) that has nuclease activity.

The present invention also relates to polynucleotides encoding a polypeptide of the present invention, as described herein. In an embodiment, the polynucleotide encoding the polypeptide, of the present invention has been isolated. One aspect relates to a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

Another aspect relates to a polypeptide having nuclease activity encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

Methods and Uses

The invention relates to the use of a nuclease of the invention to treat a fabric to provide improved softness and/or ease of ironing and/or anti-crease properties.

One aspect of the invention relates to the use of a nuclease of the invention, for treating a fabric to provide improved softness and/or ease of ironing and/or anti-crease properties.

One aspect of the invention relates to the use of a nuclease of the invention, for treating a fabric to provide improved softness properties. One aspect of the invention relates to the use of a nuclease of the invention, for treating a fabric to provide ease of ironing and/or anti-crease properties. Preferably the fabric is contacted with a liquid solution comprising the nuclease, preferably the liquid solution is a wash liquor and preferably the fabric is a cellulosic fabric.

One aspect of the invention relates to the use of a nuclease to treat a fabric to provide improved softness and/or ease of ironing and/or anti-crease properties.

One aspect of the invention relates to the use of a nuclease to treat a fabric to provide improved softness properties. One aspect of the invention relates to the use of a nuclease to treat a fabric to provide improved ease of ironing and/or anti-crease properties.

One aspect of the invention relates to the use of a nuclease to treat a fabric to provide improved softness and/or ease of ironing and/or anti-crease properties, wherein the fabric is contacted with a liquid solution comprising a polypeptide having nuclease activity.

One aspect of the invention relates to the use of a nuclease to treat a fabric to provide improved softness and/or ease of ironing and/or anti-crease properties, wherein the nuclease has DNase and RNase activity when measured in Assay I or II and Assay III respectively.

One aspect of the invention relates to the use of a nuclease to treat a fabric to provide improved softness and/or ease of ironing and/or anti-crease properties, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% RNase activity of the total nuclease activity.

One aspect of the invention relates to the use of a nuclease to treat a fabric to provide improved softness properties, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% RNase activity of the total nuclease activity.

One aspect of the invention relates to the use of a nuclease to treat a fabric to provide improved ease of ironing and/or anti-crease properties, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% RNase activity of the total nuclease activity.

One aspect of the invention relates to the use of a nuclease to treat a fabric to provide improved softness and/or ease of ironing and/or anti-crease properties, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% DNase activity of the total nuclease activity.

One aspect of the invention relates to the use of a nuclease to treat a fabric to provide improved softness properties, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% DNase activity of the total nuclease activity.

One aspect of the invention relates to the use of a nuclease to treat a fabric to provide improved ease of ironing and/or anti-crease properties, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% DNase activity of the total nuclease activity.

The present invention relates to an anti-crease or softener composition comprising a nuclease having RNase and DNase activity and to the use of such nucleases. The present invention relates to an anti-crease composition comprising a nuclease having RNase and DNase activity and to the use of such nucleases. The present invention relates to a softener composition comprising a nuclease having RNase and DNase activity and to the use of such nucleases. The composition is preferably a detergent composition, such as a fabric softener or an additive comprising a nuclease. In one aspect, the nuclease having RNase and DNase activity or a composition comprising such nuclease reduces crease formation in laundered fabrics by at least 10 percent, at least 20 percent, at least 30 percent, at least 40 percent, at least 50 percent, at least 60 percent, at least 70 percent, more preferably at least 80 percent, even more preferably at least 90 percent, compared to the fabric laundered without the nuclease or the composition.

One aspect of the invention relates to the use of a nuclease to treat a fabric to provide improved softness and/or ease of ironing and/or anti-crease properties, wherein the ratio of RNase versus DNase activity ranging from 1:10 to 10:1, preferably 1:2 to 2:1.

One aspect of the invention relates to the use of a nuclease to treat a fabric to provide improved softness properties, wherein the ratio of RNase versus DNase activity ranging from 1:10 to 10:1, preferably 1:2 to 2:1.

One aspect of the invention relates to the use of a nuclease to treat a fabric to provide improved ease of ironing and/or anti-crease properties, wherein the ratio of RNase versus DNase activity ranging from 1:10 to 10:1, preferably 1:2 to 2:1.

The use of nuclease of the invention can impart to the item a reduced tendency to get creased subsequent to e.g. washing or drying.

A preferred method of measuring crease reduction is by using the American Association of Textile Chemists and Colorists' (AATCC) method #124 as described in Example 3, the untreated fabric is given an outset score between 1 (very creased) and 5 (completely smooth). Thus, a fabric with an outset score of 5 cannot be further improved. Improvements are indicated as positive delta-score values. A delta-score value of ≥0.25 between nuclease treated and non-treated fabric is in the present context an anti-crease effect with a confidence level of P≥0.99.

In one aspect, the crease of fabric is improved with at least a 0.25 delta-score when treated with a nuclease according to the invention or in other words the anti-crease effect of a nuclease of the invention to a fabric having an out-set score of 1 to 4.75 is at least a delta score 0.25.

One aspect of the invention relates to the use of a nuclease to treat a fabric to provide improved softness and/or ease of ironing and/or anti-crease properties, wherein the delta-score value is between 0.25 and 3.75, for the fabric treated with the nuclease, when the outset score of the fabric is between 1 and 4.75 and when the anti-crease effects is measured as described in Example 3. One aspect of the invention relates to the use of a nuclease to treat a fabric to provide improved ease of ironing and/or anti-crease properties, wherein the delta-score value is between 0.25 and 3.75, for the fabric treated with the nuclease, when the outset score of the fabric is between 1 and 4.75 and when the anti-crease effects is measured as described in Example 3.

One aspect of the invention relates to the use of a nuclease to treat a fabric to provide improved softness and/or ease of ironing and/or anti-crease properties, wherein the delta-score value is 0.25, 0.50, 0.75, 1.00, 1.25, 1.50, 1.75, 2.00, 2.25, 2.50, 2.75, 3.00, 3.25, 3.50 or 3.75, for the fabric treated with the nuclease, when the outset score of the fabric is 1 to 4.75 and when the anti-crease effects is measured as described in Example 3.

The anti-crease effect or a softening effect may also be measured with the use of panelists as described in Example 4.

In one aspect, the anti-crease effect ratio of panelists preferring fabrics washed with nuclease vs test panelists preferring fabrics washed without nuclease is at least 60:40, preferably at least 65:35 preferably at least 70:30 preferably at least 75:25 preferably at least 80:20 preferably at least 85:15 preferably at least 90:10 or preferably at least 95:5, when measured as described in Example 4.

In one aspect, the improved softness effect ratio of test panelists preferring fabrics washed with nuclease vs test panelists preferring fabrics washed without nuclease is at least 60:40, preferably at least 65:35 preferably at least 70:30 preferably at least 75:25 preferably at least 80:20 preferably at least 85:15 preferably at least 90:10 or preferably at least 95:5, when measured as described in Example 4.

One aspect of the invention relates to the use of a nuclease to treat a fabric to provide improved softness and/or ease of ironing and/or anti-crease properties, wherein the anti-crease effect ratio of test panelists preferring fabrics washed with nuclease vs test panelists preferring fabrics washed without DNase is at least 60:40, preferably at least 70:30, preferably at least 80:20 or preferably at least 90:10, when measured as described in Example 4.

One aspect of the invention relates to the use of a nuclease to treat a fabric to provide improved anti-crease properties, wherein the anti-crease effect ratio of test panelists preferring fabrics washed with nuclease vs test panelists preferring fabrics washed without DNase is at least 60:40, preferably at least 70:30, preferably at least 80:20 or preferably at least 90:10, when measured as described in Example 4.

One aspect of the invention relates to the use of a nuclease to treat a fabric to provide improved softness and/or ease of ironing and/or anti-crease properties, wherein the improved softness effect ratio of test panelists preferring fabrics washed with nuclease vs test panelists preferring fabrics washed without DNase is at least 60:40, preferably at least 70:30, preferably at least 80:20 or preferably at least 90:10, when measured as described in Example 4.

One aspect of the invention relates to the use of a polypeptide having nuclease activity and has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2 for treating a fabric to provide improved softness and/or ease of ironing and/or anti-crease properties. Preferably the fabric is contacted with a liquid solution comprising the polypeptide, preferably the liquid solution is a wash liquor and preferably the fabric is a cellulosic fabric.

The invention further provides a method comprising a nuclease of the invention for reducing creases that may be formed when fabrics are washed and dried. The method includes the step of contacting the fabric with a composition, such as a detergent composition or fabric softener, that comprises a nuclease of the invention. The method is suitable for reducing creases of fabrics such as clothes. The method is suitable for reducing creases of man-made textiles such as towels, socks, T-shirts, shirts, skirts etc.

One aspect of the invention relates to a method for modifying a fabric material comprising;
(a) treating the fabric with a composition of the invention or a nuclease having RNase and DNase activity; and
(b) under conditions leading to a modified fabric, wherein the modified fabric possesses a fabric improvement compared to the unmodified fabric.

One aspect of the invention relates to a method for modifying a fabric material comprising;
(a) treating the fabric with a polypeptide, having nuclease activity and has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2; and
(b) under conditions leading to a modified fabric, wherein the modified fabric possesses a fabric improvement compared to the unmodified fabric.

Another aspect relates to method for preventing or reducing creases and/or improving softness of a fabric comprising the steps of:
a) contacting the fabric with a nuclease having DNase and RNase activity or a composition comprising such nuclease; and
b) optionally rinsing the fabric.

Preferably, the method includes further comprises washing the fabric and preferably the fabric is rinsed after being contacted with the composition or nuclease of step a).

Preferably, the nuclease applicable in any of the methods above has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% RNase activity of the total nuclease activity.

Preferably, the nuclease applicable in any of the methods above has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% DNase activity of the total nuclease activity.

Another aspect relates to method for preventing or reducing creases and/or improving softness of a fabric comprising the steps of:
a) contacting the fabric with a polypeptide, having nuclease activity and has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2; and
b) optionally rinsing the fabric.

Another aspect relates to method for preventing or reducing creases of a fabric comprising the steps of:
a) contacting the fabric with a polypeptide, having nuclease activity and has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2; and
b) optionally rinsing the fabric.

Preferably, the method includes further comprises washing the fabric and preferably the fabric is rinsed after being contacted with the composition of step a). The methods are preferably a laundry method comprising the steps of:
a) adding a composition or an additive comprising nuclease having at least 60% at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO 3,
b) optionally rinsing the item.

The laundering method includes machine wash and manual wash. The laundering process is preferably carried out at temperatures from 5° C. to 90° C., preferably from 15° C. to 60° C., such as from 20° C. to 60° C., such as from 20° C. to 40° C., such as from 30° C. to 60° C., such as from 30° C. to 40° C., such as from 50° C. to 60° C. The nuclease is preferably added in an amount corresponding to range of 0.00001-1000 ppm enzyme protein, such as in the range of 0.00001-100 enzyme protein, such as in the range of 0.00002-100 enzyme protein, such as in the range of 0.00002-1000 enzyme protein, in the range of 0.0001-1000 enzyme protein, in the range of 0.0001-100 enzyme protein, in the range of 0.0002-1000 enzyme protein, in the range of 0.0002-100 enzyme protein, in the range of 0.0004-1000 enzyme protein, in the range of 0.0004-100 enzyme protein, in the range of 0.0008-1000 enzyme protein, in the range of 0.0008-100 enzyme protein, in the range of 0.001-1000 ppm enzyme protein, in the range of 0.001-1000 ppm enzyme protein, in the range of 0.001-100 ppm enzyme protein, in the range of 0.01-1000 ppm enzyme protein, in the range of 0.01-1000 ppm enzyme protein, in the range of 0.01-100 ppm enzyme protein, in the range of 0.1-1000 ppm enzyme protein, in the range of 1-1000 ppm enzyme protein, in the range of 2-1000 ppm enzyme protein, in the range of 0.05-50 ppm enzyme protein, in the range of 0.1-50 ppm enzyme protein, in the range of 2-50 ppm enzyme protein, in the range of 0.1-30 ppm enzyme protein, in the range of 0.5-20 ppm enzyme protein, in the range of 0.5-10 ppm or in the range of 1-100 ppm enzyme protein. Preferably, the nuclease concentration in the composition of the invention e.g. in the detergent is in the range of 0.00001 ppm to 10 ppm, such as from 0.00001 ppm to 1000 ppm, such as from 0.001 ppm to 1000 ppm, such as from 0.1 ppm to 1000 ppm, such as from 1 ppm to 1000 ppm, such as from 10 ppm to 1000 ppm, such as from 0.00002 ppm to 10 ppm, such as from 0.0001 ppm to 1.00 ppm, such as from 0.0002 ppm to 1.00 ppm, such as from 0.0002 ppm to 100 ppm, such as from 0.2 ppm to 100 ppm, such as from 0.001 ppm to 0.05 ppm, such as from 0.002 ppm to 0.05 ppm, such as from 0.02 ppm to 0.1 ppm, such as from 0.05 ppm to 0.1 ppm, such as from 0.1 ppm to 0.05 ppm, such as from 0.05 ppm to 10 ppm, such as from 0.1 ppm to 10 ppm, such as from 0.1 ppm to 100 ppm, such as from 1 ppm to 100 ppm or such as from 1 ppm to 10 ppm enzyme protein. The softness of the fabric is reduced gradually after several washes. One embodiment of the invention relates to a method for treating a fabric under industrial and institutional fabric care conditions to impart anti-crease and/or softness effect. The method is suitable for laundering various fabric items. In one particular embodiment, the item is a cellulosic item such as cotton. Cotton materials are prone to creases during a washing process such as laundering and drying. In cellulosic fabric hydrogen bonds between the cellulose fibres may to some extend ensure that the fabric does not creases. However, hydrogen bonds are weak and can easily be broken down/re-arranged during wash resulting in laundry which is creased. However, also non-cellulosic textiles get creased during washing and drying.

A nuclease of the invention can impart to the item a reduced tendency to get creased subsequent to e.g. washing or drying.

Enzyme Compositions

The present invention also relates to compositions comprising a nuclease of the present invention. One aspect of the invention relates to a composition comprising nuclease having DNase and RNase. One aspect, relates to a composition comprising a nuclease, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% RNase activity of the total nuclease activity.

One aspect, relates to a composition comprising a nuclease, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% DNase activity of the total nuclease activity.

One aspect of the invention relates to a composition comprising a polypeptide, which has nuclease activity, of the invention. One aspect relates to a polypeptide having nuclease activity and which has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2.

Preferably the composition comprises one or more adjunct ingredient.

One aspect of the invention relates to a composition comprising nuclease having DNase and RNase activity, wherein the composition further comprises;
(a) one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
(b) optionally one or more enzyme, preferably selected from proteases, amylases or lipases,
(c) optionally one or more surfactant, preferably selected from anionic and nonionic surfactants, and
(d) optionally one or more polymer.

In one aspect, the composition comprises a polymer, wherein the polymer is preferably poly(vinylimidazole) (PVI), poly(vinylpyridine-N-oxide) (PVPO or PVPNO), polyvinylpyrrolidone-vinylimidazole (PVPVI) or an amphiphilic carboxyalkylated polyamine (as described in WO2017/129424).

One aspect of the invention relates a composition comprising nuclease having DNase and RNase activity, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% RNase activity of the total nuclease activity and wherein the composition further comprises;
(a) one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
(b) optionally one or more enzyme, preferably selected from proteases, amylases or lipases,
(c) optionally one or more surfactant, preferably selected from anionic and nonionic surfactants, and
(d) optionally one or more polymer.

One aspect of the invention relates a composition comprising nuclease having DNase and RNase activity, wherein the nuclease has at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, but less than 100% DNase activity of the total activity and wherein the composition further comprises;
(a) one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
(b) optionally one or more enzyme, preferably selected from proteases, amylases or lipases,
(c) optionally one or more surfactant, preferably selected from anionic and nonionic surfactants, and
(d) optionally one or more polymer.

One aspect of the invention relates to a composition comprising a polypeptide having at least at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2, which has nuclease activity, wherein the composition further comprises;
(a) one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol,
(b) optionally one or more enzyme, preferably selected from proteases, amylases or lipases,
(c) optionally one or more surfactant, preferably selected from anionic and nonionic surfactants, and
(d) optionally one or more polymer.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, endoglucanase, esterase, glucoamylase, invertase, laccase, lipase, mannosidase, mutanase, oxidase, pectinolytic enzyme, peroxidase, phytase, polyphenoloxidase, proteolytic enzyme, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

The composition comprising a nuclease of the present invention preferably comprises in addition to the nuclease one or more additional cleaning composition components. The choice of additional components is within the skill of the artisan and includes conventional ingredients, including the exemplary non-limiting components set forth below.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein, the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein, the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein, the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein, the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein, the detergent will usually contain from about 0% to about 40% by weight of a zwitterionic surfactant. Non-limiting examples of zwitterionic surfactants include betaines such as alkyldimethylbetaines, sulfobetaines, and combinations thereof.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. The builder and/or co-builder may particularly be a chelating agent that forms water-soluble complexes with Ca and Mg. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N,N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(0)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

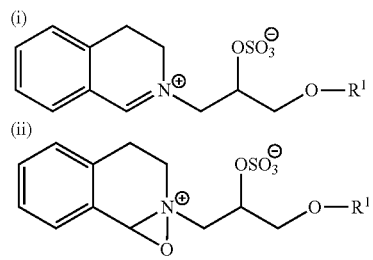

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning, anti-crease properties and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO), polyvinylpyrrolidone-vinylimidazole (PVPVI) and amphiphilic carboxyalkylated polyamine as described in WO2017/129424. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO 2007/087243.

Enzymes

The detergent additive as well as the detergent composition may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO: 2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™ and Puradax HA™ (Genencor International Inc.), and KAC-500(B)™ (Kao Corporation).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867, and Subtilisin lentus, Subtilisin Novo, subtilisin Carlsberg, *Bacillus licheniformis*, subtilisin BPN', subtilisin 309, subtilisin 147 and subtilisin 168 and e.g. protease PD138 described in (WO93/18140). Other useful proteases may be those described in WO01/016285 and WO02/016547. Examples of trypsin-like proteases are trypsin (e.g. of porcine or bovine origin) and the *Fusarium* protease described in WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Proctor & Gamble/Genencor Int.) such as those derived from *Bacillus amyloliquefaciens*.

Examples of useful proteases are the variants described in: WO89/06279 WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the protease variants may comprise one or more of the mutations selected from the group consisting of: S3T, V41, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V1021, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease shown in SEQ ID NO 1 of WO2016/001449, the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes NS), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (Bacillus alkalophilus subtilisin) from Kao.

Lipases and Cutinases:

Suitable lipases and cutinases include those of bacterial or fungal origin. Chemically modified or protein engineered mutant enzymes are included. Examples include lipase from Thermomyces, e.g. from T. lanuginosus (previously named Humicola lanuginosa) as described in EP 258068 and EP 305216, cutinase from Humicola, e.g. H. insolens (WO 96/13580), lipase from strains of Pseudomonas (some of these now renamed to Burkholderia), e.g. P. alcaligenes or P. pseudoalcaligenes (EP 218272), P. cepacia (EP 331376), P. sp. strain SD705 (WO 95/06720 & WO 96/27002), P. wisconsinensis (WO 96/12012), GDSL-type Streptomyces lipases (WO 10/065455), cutinase from Magnaporthe grisea (WO 10/107560), cutinase from Pseudomonas mendocina (U.S. Pat. No. 5,389,536), lipase from Thermobifida fusca (WO 11/084412), Geobacillus stearothermophilus lipase (WO 11/084417), lipase from Bacillus subtilis (WO 11/084599), and lipase from Streptomyces griseus (WO 11/150157) and S. pristinaespiralis (WO 12/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 07/87508 and WO 09/109500.

Preferred commercial lipase products include Lipolase™, Lipex™, Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to Candida antarctica lipase A (WO 10/111143), acyltransferase from Mycobacterium smegmatis (WO 05/56782), perhydrolases from the CE 7 family (WO 09/67279), and variants of the M. smegmatis perhydrolase in particular the S54V variant used in the commercial product Gentle Power Bleach from Huntsman Textile Effects Pte Ltd (WO 10/100028).

Amylases:

Suitable amylases which can be used together with the nuclease may be an alpha-amylase or a glucoamylase and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from B. amyloliquefaciens shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476. Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+ G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO2011/098531, WO2013/001078 and WO2013/001087. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases:

A peroxidase according to be included in compositions according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity. Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257. Peroxidases includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. The haloperoxidase may be a chloroperoxidase. Preferably, the haloperoxidase is a vanadium haloperoxidase, i.e., a vanadate-containing haloperoxidase. Preferably, the vanadate-containing haloperoxidase is combined with a source of chloride ion. Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*. Haloperoxidases have also been isolated from bacteria such as *Pseudomonas*, e.g., *P. pyrrocinia* and *Streptomyces*, e.g., *S. aureofaciens*. Preferably the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460. Oxidases include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be obtained from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase obtained from *Coprinopsis* or *Myceliophthora* is preferred; in particular, a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Other Materials

Any detergent components known in the art for use in detergents may also be utilized. Other optional detergent components include anti-corrosion agents, anti-shrink agents, anti-soil re-deposition agents, anti-wrinkling agents, bactericides, fungicides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Anti-Static Agents

The detergent compositions of the present invention may also include one or more anti-static agents. Common anti-static agents are based on long-chain aliphatic amines (optionally ethoxylated) and amides, quaternary ammonium salts (e.g., behentrimonium chloride or cocamidopropyl betaine), esters of phosphoric acid, polyethylene glycol esters, or polyols. Indium tin oxide can be used as transparent anti-static coating of windows. It is also possible to use conductive polymers, like PEDOT:PSS and conducting polymer nanofibers, particularly polyaniline nanofibers. One group of anti-static compounds are the methanesulfonamide anti-static agents substituted on the nitrogen atom and having the formula: $RNHSO_2CH_3$, wherein R is a secondary aliphatic hydrocarbon chain containing at least 8 carbons. The methanesulfonamides substituted on the nitrogen atom with one secondary long aliphatic chain containing 8-22 carbons reduces or prevents the generation of static electricity on cotton and synthetic fabrics during laundering. These anti-static properties can be imparted to fabrics by laundering in a detergent composition containing said methanesulfonamides which are completely compatible with anionic, non-ionic, cationic and amphoteric detergents. This same treatment has been found to additionally confer a soft hand on cotton fabrics. These beneficial effects are achieved without yellowing or discoloration of the fabrics and without interference with the action of optical brighteners that may be present in the detergent composition. Another group of anti-static compounds are cationic quaternary ammonium compounds as described in WO2008/000333, WO95/29218, WO2011/011247 or WO2009/158388.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The nuclease may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising a nuclease of the invention. The granule is composed of a core, and optionally one or more coatings (outer layers) surrounding the core. Typically, the granule/particle size, measured as equivalent spherical diameter (volume based average particle size), of the granule is 20-2000 µm, particularly 50-1500 µm, 100-1500 µm or 250-1200 µm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 µm, particularly 50-1500 µm, 100-1500 µm or 250-1200 µm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation. Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606. The coating may be applied in an amount of at least 0.1% by weight of the core, e.g., at least 0.5%, 1% or 5%. The amount may be at most 100%, 70%, 50%, 40% or 30%. The coating is preferably at least 0.1 µm thick, particularly at least 0.5 µm, at least 1 µm or at least 5 µm. The thickness of the coating may be below 100 µm. In a more particular embodiment the thickness of the coating is below 60 µm. In an even more particular embodiment the total thickness of the coating is below 40 µm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 µm, such as less than 10 µm or less than 5 µm. The salt coating may comprise a single salt or a mixture of two or more salts. The salt may be water soluble, having a solubility at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710. Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate. The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4 \cdot 7\ H_2O$), zinc sulfate heptahydrate ($ZnSO_4 \cdot 7\ H_2O$), sodium phosphate dibasic heptahydrate ($Na_2HPO_4 \cdot 7\ H_2O$), magnesium nitrate hexahydrate ($Mg(NO_3)_2(6H_2O)$), sodium citrate dihydrate and magnesium acetate tetrahydrate. Preferably, the salt is applied as a solution of the salt, e.g., using a fluid bed. In one aspect, the present invention provides a granule, which comprises:
  (a) a core comprising a nuclease according to the invention, and
  (b) optionally a coating consisting of one or more layer(s) surrounding the core.

One aspect of the invention relates to a granule composition comprising
  a) a core comprising a nuclease, which has RNase and DNase activity and optionally,
  b) a coating consisting of one or more layer(s) surrounding the core.

One aspect of the invention relates to a granule composition comprising
  a) a core comprising a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, which has nuclease activity and optionally,
  b) a coating consisting of one or more layer(s) surrounding the core.

Laundry Soap Bars

The nuclease or the composition comprising nuclease may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two-stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, nuclease, optionally one or more additional enzymes, a protease inhibitor, and a salt of a monovalent cation and an organic anion may be prepared and the mixture is then plodded. The nuclease and optional additional enzymes may be added at the same time as the protease inhibitor for example in liquid form. Besides the mixing step and the plodding step, the process may further comprise the steps of milling, extruding, cutting, stamping, cooling and/or wrapping.

EXAMPLES

Enzyme Assays
Assay I Testing of DNase Activity

DNase activity was determined on DNase Test Agar with Methyl Green (BD, Franklin Lakes, N.J., USA), which was prepared according to the manual from the supplier. Briefly, 21 g of agar was dissolved in 500 ml water and then autoclaved for 15 min at 121° C. Autoclaved agar was temperated to 48° C. in a water bath, and 20 ml of agar was poured into petridishes and allowed to solidify by incubation overnight at room temperature. On solidified agar plates, 5 µl of enzyme solutions are added, and DNase activity is observed as colorless zones around the spotted enzyme solutions.

Assay II Testing of DNase Activity

DNase activity was determined by fluorescence using fluorescence-quenched DNA oligonucleotide probe. This probe emits signal after nuclease degradation according to the manual from the supplier (DNase alert kit, Integrated DNA Technology, Coralville, Iowa, USA). Briefly, 5 µl of the substrate was added to 95 µl of DNase. If the signal was too high, further dilutions of DNase was done in the adequate buffer. Kinetic curve was measured for 20 min at 22° C. using a Clariostar microplate reader (536 nm excitation, 556 nm emission).

Assay III: Testing of RNase Activity

RNase activity was determined by fluorescence using fluorescence-quenched oligonucleotides probe. This probe emits signal after nuclease degradation according to the manual from the supplier (RNase alert kit, Integrated DNA Technology, Coralville, Iowa, USA). Briefly, RNase was diluted in water hardness 15° dH to obtain a concentration of 2 ppm, 5 µl of the substrate was added to 95 µl of the RNase sample. Kinetic curve was measured for 10 min at 22° C. using a Clariostar microplate reader (excitation 490 nm, emission at 520 nm).

Example 1 Expression and Cloning of *Bacillus* SP-62738 DNase

The nuclease was derived from a bacterial strain isolated from environmental soil sample by standard microbiological isolation techniques. The isolated pure strain was identified and taxonomy was assigned based on DNA sequencing of the 16S ribosomal genes (Table 1).

TABLE 1

| Strain or community | Source Country | Mature protein SEQ ID: |
|---|---|---|
| *Bacillus* sp. 62738 | Denmark | 3 |

Chromosomal DNA was isolated from pure culture with the DNeasy Blood & Tissue Kit from Qiagen (Hilden, Germany) and subjected to full genome sequencing using Illumina technology. Genome sequencing, the subsequent assembly of reads and the gene discovery (i.e. annotation of gene functions) is known to the person skilled in the art and the service can be purchased commercially. The genome sequence was analyzed for putative nucleases from the PFAM database family PF13930 (R. D. Finn et al. Nucleic Acids Research (2014), 42:D222-D230) this analysis identified a gene encoding a putative nuclease which was subsequently cloned and recombinantly expressed in *Bacillus subtilis*. The gene encoding the nuclease was amplified as a single amplicon by PCR and fused with regulatory elements, affinity purification tag and homology regions for recombination into the pectate lyase locus of the *B. subtilis* genome. The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene between two *B. subtilis* chromosomal regions along with strong promoters and a chloramphenicol resistance marker. The SOE-PCR method is also described in patent application WO2003/095658. The genes were expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The genes were fused with DNA encoding a *Bacillus clausii* secretion signal (encoding the following amino acid sequence: MKKPLGKIVASTALLISVAFSS-SIASA (SEQ ID NO 4)) replacing the native secretion signal. Furthermore, the expression construct results in the addition of a carboxy-terminal poly histidine tail consisting of the amino acid sequence HHHHHH (SEQ ID NO 5) to the mature nucleases. The SOE-PCR products were transformed into *Bacillus subtilis* and integrated in the chromosome by homologous recombination into the pectate lyase locus. Subsequently a recombinant *Bacillus subtilis* clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Example 2 Purification of *Bacillus* SP-62738 DNase

Purification of the recombinant enzyme by nickel affinity chromatography. The pH of the cleared supernatant was adjusted to pH 8, filtrated through a 0.2 µM filter, and the supernatant applied to a 5 ml HisTrap™ excel column. Prior to loading, the column had been equilibrated in 5 column volumes (CV) of 50 mM Tris/HCl pH 8. In order to remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column, equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Example 3 Nuclease Anti-Crease Properties with Nucleic Acid Containing Soil from Soil Ballast Evaluated on Tracer Textile of Two Different Cotton Types In this study, 8 pieces of unsoiled cotton W80A (CFT) in size 25×35 cm$^2$, 8 pieces of unsoiled cotton CN42 (CFT) in size 25×35 cm$^2$ and 4 pieces of soil-ballast (SBL-CFT) in size 40×20 cm$^2$ equalizing 8 g soil were added to each European front loader Full Scale Wash (FSW) machine. Washes were done using Miele Softtronic W5841 washing machine (Program: Cottons; Additional program: Short; Temperature: 30° C.; Centrifuge: 1600 rpm; Ballast: 600-700 g 100% cotton T-shirts). Ariel Color & Style (commercial detergent) was dosed 5 g/L at 15° dH water hardness. Purified nuclease (SEQ ID NO 3) dosed 2 ppm was added. From each machine W80A and CN42 fabrics pieces were line-dried for 24 h at room temperature. Fabric pieces were evaluated by the internationally recognized method of measuring crease reduction using the American Association of Textile Chemists and Colorists' (AATCC) method #124: Appearance of Fabrics after Repeated Home Laundering. The dried fabrics were then evaluated for crease content by comparison with crease smoothness replicas, which can be purchased from AATCC. Factors such as the light used, the angle of the fabrics and replicas to the light and the background were carefully controlled as described in the method #124. There are six smoothness standard replicas with values of 1, 2, 3, 3.5, 4 and 5 with 5 being perfectly smooth and 1 being very creased. Three trained observers were asked to assign a value of 1-5, the nearest half number, to each fabric based on which replica it most closely resembles. The results are totaled and averaged over the three observers for each fabric type. According to the method, a difference of greater than 0.17 between the results for two test conditions indicates there is a significant difference at the 95% confidence level. A difference of greater than or equal to 0.25 indicates a significant difference at the 99% confidence level.

TABLE 2 result of observer scoring for fabrics washed with or without nuclease

| Enzyme | FSW wash conditions | Detergent | Soiled/clean Textile in the wash | Drying regime | Tracer | Textile evaluated by AATCC Smoothness standards Average SA-value according to AATCC +/− stE on average | | Delta − value |
|---|---|---|---|---|---|---|---|---|
| | | | | | | − nuclease | + nuclease | |
| Nuclease SEQ ID NO 1 (2 ppm) | Cottons; Additional program: Short; Temperature: 30° C.; Centrifuge: 1600 rpm | Ariel Color & Style | Clean W80A Clean CN 42 Soiled SBL-CFT Clean 100% cotton T-shirt ballast. | Line dry | W80A CN 42 | 1, 9 1, 7 | 3, 3 3, 3 | 1, 4 1, 6 |

Values specify the average SA value rank given by the panel according to the AATCC smoothness standards +/− StE.

Example 4 Evaluation of Nuclease Anti-Crease Properties by Panel Preference

In this study, 8 pieces of unsoiled cotton W80A (CFT) in size 25×35 cm², 8 pieces of unsoiled cotton CN42 (CFT) in size 25×35 cm² and 4 pieces of soil-ballast (SBL-CFT) in size 40×20 cm² equalizing 8 g soil were added to each European front loader Full Scale Wash (FSW) machine. Washes were done using Miele Softtronic W5841 washing machine (Program: Cottons; Additional program: Short; Temperature: 30° C.; Water hardness: 15° dH; Centrifuge: 1600 rpm; Ballast: 600-700 g 100% cotton T-shirts). Ariel Color & Style was dosed 5 g/L. Purified nuclease (SEQ ID NO 3) dosed 2 ppm was added to half the machines. From each machine W80A and CN42 fabrics pieces were line-dried for 24 h at room temperature. All respective textile pieces washed without and with nuclease were collected, randomly paired and evaluated by a panel consisting of 2-4 panelists. Panelists were asked to select the piece of textile of the pair being the less creased. After evaluation, distribution was calculated.

TABLE 3

Panel score for fabrics washed with vs without nuclease.

| | Wash program | Detergent | W80A cotton | CN-42 cotton |
|---|---|---|---|---|
| Nuclease (2 ppm) | Short cotton wash, 30° C., 15° dH water | Ariel Color and style | 87:13 | 69:31 |

First number specifies the % that prefers textile pieces washed with nuclease, whereas the second number specifies the % that prefers real item washed without nuclease.

The invention claimed is:

1. A composition comprising nuclease having DNase and RNase activity, wherein the composition further comprises; (a) one or more polyol(s), selected from glycerol, (mono, di, or tri) propylene glycol, ethylene glycol, polyethylene glycol, sugar alcohols, sorbitol, mannitol, erythritol, dulcitol, inositol, xylitol and adonitol, (b) one or more enzyme(s), selected from proteases, amylases or lipases, (c) one or more surfactant(s), selected from anionic and nonionic surfactants, and (d) one or more polymers.

2. The composition of claim 1, wherein the polymer is poly(vinylimidazole) (PVI), poly(vinylpyridine-N-oxide) (PVPO or PVPNO), polyvinylpyrrolidone-vinylimidazole (PVPVI) or an amphiphilic carboxyalkylated polyamine.

3. The composition of claim 1, wherein the nuclease has at least 10% but less than 100% RNase activity.

4. A method for modifying a fabric material comprising (a) treating the fabric with the composition of claim 1; (b) under conditions leading to a modified fabric, wherein the modified fabric possesses a fabric improvement compared to the unmodified fabric.

5. A method for preventing or reducing creases and/or improving softness of a fabric comprising the steps of: a) contacting the fabric with the composition of claim 1; and b) rinsing the fabric.

6. The method of claim 4, wherein the nuclease has at least 10% but less than 100% RNase activity of the total nuclease activity.

7. The method of claim 4, wherein the nuclease has at least 80% sequence identity to the polypeptide comprising the amino acid sequence of SEQ ID NO 2.

* * * * *

SEQUENCE LISTING

```
<160> NUMBER OF SEQ ID NOS: 5

<210> SEQ ID NO 1
<211> LENGTH: 789
<212> TYPE: DNA
<213> ORGANISM: Bacillus sp-62738
<220> FEATURE:
<221> NAME/KEY: CDS
<222> LOCATION: (1)..(786)
<220> FEATURE:
<221> NAME/KEY: sig_peptide
<222> LOCATION: (1)..(93)
<220> FEATURE:
<221> NAME/KEY: mat_peptide
<222> LOCATION: (94)..(786)

<400> SEQUENCE: 1 atg aaa ctt aaa aca aca ctt ata aaa tcc att tca att atc gca gca     48
Met Lys Leu Lys Thr Thr Leu Ile Lys Ser Ile Ser Ile Ile Ala Ala
    -30                 -25                 -20 agt atg atg ctg gga gct tgt agt cct cct tct aat gct agt tcc agt     96
Ser Met Met Leu Gly Ala Cys Ser Pro Pro Ser Asn Ala Ser Ser Ser
-15                 -10                  -5                 -1   1 acg aat aaa caa gaa cca tct caa gct acc acg aaa caa gaa tct aat    144
```

```
        Thr Asn Lys Gln Glu Pro Ser Gln Ala Thr Thr Lys Gln Glu Ser Asn
                      5                  10                  15 cag act caa aat aag act tct aac ggc caa caa cag tct tat aac ata      192
Gln Thr Gln Asn Lys Thr Ser Asn Gly Gln Gln Gln Ser Tyr Asn Ile
             20                  25                  30 gag gac att gca aag aac tac aaa ggt caa aaa gta gta gaa ata aac      240
Glu Asp Ile Ala Lys Asn Tyr Lys Gly Gln Lys Val Val Glu Ile Asn
 35                  40                  45 gga aat aaa gct gat ttt aca caa gat caa tta gat aaa gta cag ttg      288
Gly Asn Lys Ala Asp Phe Thr Gln Asp Gln Leu Asp Lys Val Gln Leu
 50                  55                  60                  65 aag aat aca aat cct aca tgg caa gag ttc tct aac tta gat agt aag      336
Lys Asn Thr Asn Pro Thr Trp Gln Glu Phe Ser Asn Leu Asp Ser Lys
                 70                  75                  80 aac aga gtt gga gta gca aca gca tta att ggt aaa gaa att caa cct      384
Asn Arg Val Gly Val Ala Thr Ala Leu Ile Gly Lys Glu Ile Gln Pro
             85                  90                  95 aaa gaa aaa cga gat gag aga ttg aat aca aaa cct act ggt tgg cat      432
Lys Glu Lys Arg Asp Glu Arg Leu Asn Thr Lys Pro Thr Gly Trp His
        100                 105                 110 caa aag aaa tta agt gat ggt agt aca ttg ttt gat aga agt cat tta      480
Gln Lys Lys Leu Ser Asp Gly Ser Thr Leu Phe Asp Arg Ser His Leu
    115                 120                 125 att gga tat caa cta act ggt caa aac gac aat ccc aag aat tta atg      528
Ile Gly Tyr Gln Leu Thr Gly Gln Asn Asp Asn Pro Lys Asn Leu Met
130                 135                 140                 145 act ggt aca aaa gat ttt aac cga cat agt atg tta aag tat gaa aac      576
Thr Gly Thr Lys Asp Phe Asn Arg His Ser Met Leu Lys Tyr Glu Asn
                150                 155                 160 atg gta gat aaa gag gtt gaa aaa gga agt tat gta ctt tac gaa gta      624
Met Val Asp Lys Glu Val Glu Lys Gly Ser Tyr Val Leu Tyr Glu Val
            165                 170                 175 aaa cca gta ttt atc ggt gac gag tta gtc gca aga ggt gta caa atg      672
Lys Pro Val Phe Ile Gly Asp Glu Leu Val Ala Arg Gly Val Gln Met
        180                 185                 190 aaa gcg aaa acg gtt aat aat aat cac tta gat ttc aac gta ttc tgt      720
Lys Ala Lys Thr Val Asn Asn Asn His Leu Asp Phe Asn Val Phe Cys
    195                 200                 205 ttt aat gtg caa gat ggt gta gag att gac tat aaa gat ggt act tct      768
Phe Asn Val Gln Asp Gly Val Glu Ile Asp Tyr Lys Asp Gly Thr Ser
210                 215                 220                 225 aaa cta gtt aat aaa caa taa                                          789
Lys Leu Val Asn Lys Gln
                230

<210> SEQ ID NO 2
<211> LENGTH: 262
<212> TYPE: PRT
<213> ORGANISM: Bacillus sp-62738

<400> SEQUENCE: 2

Met Lys Leu Lys Thr Thr Leu Ile Lys Ser Ile Ser Ile Ile Ala Ala
        -30                 -25                 -20

Ser Met Met Leu Gly Ala Cys Ser Pro Pro Ser Asn Ala Ser Ser Ser
    -15                 -10                  -5              -1  1

Thr Asn Lys Gln Glu Pro Ser Gln Ala Thr Thr Lys Gln Glu Ser Asn
              5                  10                  15

Gln Thr Gln Asn Lys Thr Ser Asn Gly Gln Gln Gln Ser Tyr Asn Ile
         20                  25                  30
```

```
Glu Asp Ile Ala Lys Asn Tyr Lys Gly Gln Lys Val Val Glu Ile Asn
     35                  40                  45
Gly Asn Lys Ala Asp Phe Thr Gln Asp Gln Leu Asp Lys Val Gln Leu
 50                  55                  60                  65
Lys Asn Thr Asn Pro Thr Trp Gln Glu Phe Ser Asn Leu Asp Ser Lys
                 70                  75                  80
Asn Arg Val Gly Val Ala Thr Ala Leu Ile Gly Lys Glu Ile Gln Pro
                 85                  90                  95
Lys Glu Lys Arg Asp Glu Arg Leu Asn Thr Lys Pro Thr Gly Trp His
            100                 105                 110
Gln Lys Lys Leu Ser Asp Gly Ser Thr Leu Phe Asp Arg Ser His Leu
        115                 120                 125
Ile Gly Tyr Gln Leu Thr Gly Gln Asn Asp Asn Pro Lys Asn Leu Met
130                 135                 140                 145
Thr Gly Thr Lys Asp Phe Asn Arg His Ser Met Leu Lys Tyr Glu Asn
                150                 155                 160
Met Val Asp Lys Glu Val Glu Lys Gly Ser Tyr Val Leu Tyr Glu Val
            165                 170                 175
Lys Pro Val Phe Ile Gly Asp Glu Leu Val Ala Arg Gly Val Gln Met
        180                 185                 190
Lys Ala Lys Thr Val Asn Asn Asn His Leu Asp Phe Asn Val Phe Cys
    195                 200                 205
Phe Asn Val Gln Asp Gly Val Glu Ile Asp Tyr Lys Asp Gly Thr Ser
210                 215                 220                 225
Lys Leu Val Asn Lys Gln
                230

<210> SEQ ID NO 3
<211> LENGTH: 231
<212> TYPE: PRT
<213> ORGANISM: Bacillus sp-62738

<400> SEQUENCE: 3

Ser Thr Asn Lys Gln Glu Pro Ser Gln Ala Thr Thr Lys Gln Glu Ser
 1               5                  10                  15
Asn Gln Thr Gln Asn Lys Thr Ser Asn Gly Gln Gln Ser Tyr Asn
             20                  25                  30
Ile Glu Asp Ile Ala Lys Asn Tyr Lys Gly Gln Lys Val Val Glu Ile
             35                  40                  45
Asn Gly Asn Lys Ala Asp Phe Thr Gln Asp Gln Leu Asp Lys Val Gln
         50                  55                  60
Leu Lys Asn Thr Asn Pro Thr Trp Gln Glu Phe Ser Asn Leu Asp Ser
 65                  70                  75                  80
Lys Asn Arg Val Gly Val Ala Thr Ala Leu Ile Gly Lys Glu Ile Gln
                 85                  90                  95
Pro Lys Glu Lys Arg Asp Glu Arg Leu Asn Thr Lys Pro Thr Gly Trp
            100                 105                 110
His Gln Lys Lys Leu Ser Asp Gly Ser Thr Leu Phe Asp Arg Ser His
        115                 120                 125
Leu Ile Gly Tyr Gln Leu Thr Gly Gln Asn Asp Asn Pro Lys Asn Leu
130                 135                 140
Met Thr Gly Thr Lys Asp Phe Asn Arg His Ser Met Leu Lys Tyr Glu
145                 150                 155                 160
Asn Met Val Asp Lys Glu Val Glu Lys Gly Ser Tyr Val Leu Tyr Glu
                165                 170                 175
```

```
Val Lys Pro Val Phe Ile Gly Asp Glu Leu Val Ala Arg Gly Val Gln
            180                 185                 190

Met Lys Ala Lys Thr Val Asn Asn Asn His Leu Asp Phe Asn Val Phe
            195                 200                 205

Cys Phe Asn Val Gln Asp Gly Val Glu Ile Asp Tyr Lys Asp Gly Thr
            210                 215                 220

Ser Lys Leu Val Asn Lys Gln
225                 230

<210> SEQ ID NO 4
<211> LENGTH: 27
<212> TYPE: PRT
<213> ORGANISM: Artificial
<220> FEATURE:
<223> OTHER INFORMATION: Signal peptide

<400> SEQUENCE: 4

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 5
<211> LENGTH: 6
<212> TYPE: PRT
<213> ORGANISM: Artificial
<220> FEATURE:
<223> OTHER INFORMATION: His-tag

<400> SEQUENCE: 5

His His His His His His
1               5
```